(12) United States Patent
Buczynski

(10) Patent No.: US 8,865,087 B2
(45) Date of Patent: Oct. 21, 2014

(54) STEAM STERILIZER

(75) Inventor: Peter J. Buczynski, Girard, PA (US)

(73) Assignee: American Sterilizer Company, Mentor, OH (US)

( * ) Notice: Subject to any disclaimer, the term of this patent is extended or adjusted under 35 U.S.C. 154(b) by 592 days.

(21) Appl. No.: 13/252,606

(22) Filed: Oct. 4, 2011

(65) Prior Publication Data

US 2013/0084225 A1    Apr. 4, 2013

(51) Int. Cl.
  *A61L 2/00*    (2006.01)
  *A61L 2/07*    (2006.01)

(52) U.S. Cl.
  CPC .......................................... *A61L 2/07* (2013.01)
  USPC .......................................................... 422/292

(58) Field of Classification Search
  USPC .......................................................... 422/292
  See application file for complete search history.

(56) References Cited

U.S. PATENT DOCUMENTS

| | | | |
|---|---|---|---|
| 3,717,434 A | 2/1973 | Black | 21/94 |
| 3,861,873 A | 1/1975 | MacFarlane et al. | 21/56 |
| 4,108,601 A | 8/1978 | Wolff | 21/96 |
| 4,203,947 A * | 5/1980 | Young et al. | 422/114 |
| 4,263,258 A | 4/1981 | Kalasek | 422/113 |
| 4,497,773 A | 2/1985 | Kuelzow et al. | 422/26 |
| 4,808,377 A | 2/1989 | Childers et al. | 422/26 |
| 5,424,047 A | 6/1995 | Zwingenberger et al. | 422/296 |
| 5,858,304 A | 1/1999 | Breach | 422/26 |
| 6,094,523 A | 7/2000 | Zelina et al. | 392/399 |
| 6,797,233 B1 * | 9/2004 | De Heus | 422/26 |
| 7,079,759 B2 | 7/2006 | Tokutake et al. | 392/394 |
| 7,138,087 B1 | 11/2006 | Malkin et al. | 422/26 |
| 2006/0057021 A1 | 3/2006 | Sawyer et al. | 422/26 |
| 2010/0247388 A1 | 9/2010 | Buczynski et al. | 422/112 |

FOREIGN PATENT DOCUMENTS

EP    0818205    1/1998    ............... A61L 2/06

* cited by examiner

*Primary Examiner* — Kevin Joyner
(74) *Attorney, Agent, or Firm* — Kusner & Jaffe; Michael A. Centanni

(57) ABSTRACT

A sterilizer for sterilizing instruments and devices disposed therein. The sterilizer includes a vessel that has an inner wall and an outer wall. The inner wall defines a sterilization chamber. The outer wall is spaced from the inner wall to define a cavity surrounding the sterilization chamber. A heating element for vaporizing a fluid is disposed in a lower portion of the cavity. A fluid circuit is fluidly connected to the vessel to convey fluid to the cavity, to convey steam from the cavity to the sterilization chamber and to exhaust steam from the sterilization chamber. The fluid circuit includes a conduit that fluidly connects the sterilization chamber to the cavity. A valve is disposed in the conduit for controlling the flow of steam from the cavity to the sterilization chamber. A boiler pump is provided for conveying fluid to the cavity of the vessel.

4 Claims, 3 Drawing Sheets

STEAM STERILIZER

FIELD OF THE INVENTION

The present invention relates generally to sterilizers and, more particularly, to a steam sterilizer for medical, dental, and surgical equipment and will be discussed with particular reference thereto.

BACKGROUND OF THE INVENTION

Steam sterilizers are widely used in hospitals, laboratories, and other facilities to sterilize many types of items. A typical steam sterilizer includes a chamber to receive the items to be sterilized and a steam jacket that surrounds the chamber. The steam sterilizer exposes the items in the chamber to heated steam during a steam sterilization cycle.

The temperature and pressure of the steam must meet specific requirements during critical phases of the steam sterilization cycle in order for the items to be sterilized. In particular, the steam in the chamber must be maintained within a predetermined temperature range(s) during critical phases of the steam sterilization cycle. If the temperature of the steam in the chamber falls below the predetermined temperature range(s), the items in the steam sterilizer may not be properly sterilized.

The steam jacket of the steam sterilizer is designed to maintain the temperature of the steam in the chamber within the predetermined temperature range(s) during critical phases of the steam sterilization cycle. The chamber and the steam jacket usually are supplied with steam from a steam generator or from another source of steam in the facility. A typical steam generator includes a boiler for vaporizing water to form steam. A plurality of conduits connects the boiler to the chamber and to the steam jacket of the steam sterilizer.

In most instances, the boiler and the plurality of conduits are covered with insulation. However, even the best insulation will allow some heat to be lost to the surrounding environment. Heat loss from the boiler and from the plurality of conduits increases the risk that the temperature in the chamber of the sterilizer will fall below the predetermined temperature range(s) during critical phases of the steam sterilization cycle.

The present invention provides a steam sterilizer wherein water is vaporized in a steam jacket surrounding a chamber of the steam sterilizer to more efficiently heat the chamber and to reduce the likelihood that heat will be lost to the surrounding environment during a steam sterilization cycle.

SUMMARY OF THE INVENTION

In accordance with a preferred embodiment of the present invention, there is provided a steam sterilizer for sterilizing instruments and devices disposed therein. The sterilizer includes a vessel that has an inner wall and an outer wall. The inner wall defines a sterilization chamber. The outer wall is spaced from the inner wall to define a cavity surrounding the sterilization chamber. A heating element for vaporizing water is disposed in a lower portion of the cavity. A fluid circuit is fluidly connected to the vessel to convey fluid to the cavity, to convey steam from the cavity to the sterilization chamber and to exhaust steam from the sterilization chamber. The fluid circuit includes a conduit that fluidly connects the sterilization chamber to the cavity. A valve is disposed in the conduit for controlling the flow of steam from the cavity to the sterilization chamber. A boiler pump is provided for conveying fluid to the cavity of the vessel.

An advantage of the present invention is a steam sterilizer for sterilizing medical items and the like.

Another advantage of the present invention is a steam sterilizer having a cavity surrounding a chamber of the steam sterilizer.

Another advantage of the present invention is a steam sterilizer as described above having a heating element disposed within the cavity.

Another advantage of the present invention is a steam sterilizer as described above wherein water is vaporized within the cavity surrounding the chamber of the steam sterilizer.

Another advantage of the present invention is a steam sterilizer as described above that reduces the likelihood of heat loss to the surrounding environment during critical phases of a steam sterilization cycle.

These and other advantages will become apparent from the following description of a preferred embodiment taken together with the accompanying drawings and the appended claims.

BRIEF DESCRIPTION OF THE DRAWINGS

The invention may take physical form in certain parts and arrangement of parts, a preferred embodiment of which will be described in detail in the specification and illustrated in the accompanying drawings which form a part hereof, and wherein.

DETAILED DESCRIPTION OF PREFERRED EMBODIMENT

Figure 1:
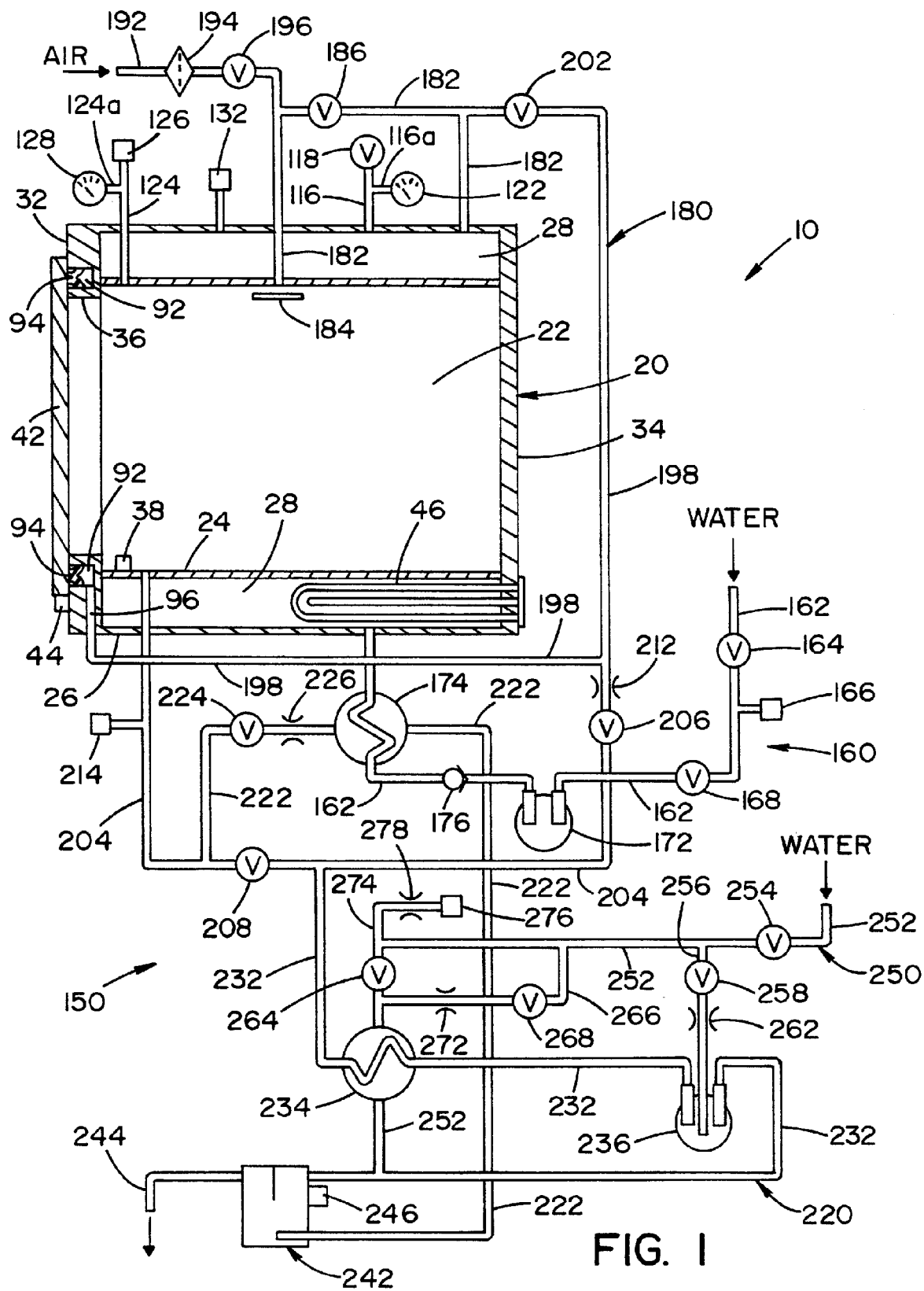
FIG. 1 is a schematic view of a steam sterilizer according to the present invention.

Referring now to the drawings wherein the showings are for the purpose of illustrating a preferred embodiment of the invention only and not for the purpose of limiting same, FIG. 1 shows a schematic view of steam sterilizer 10 for sterilizing medical instruments and other items.

Figure 3:
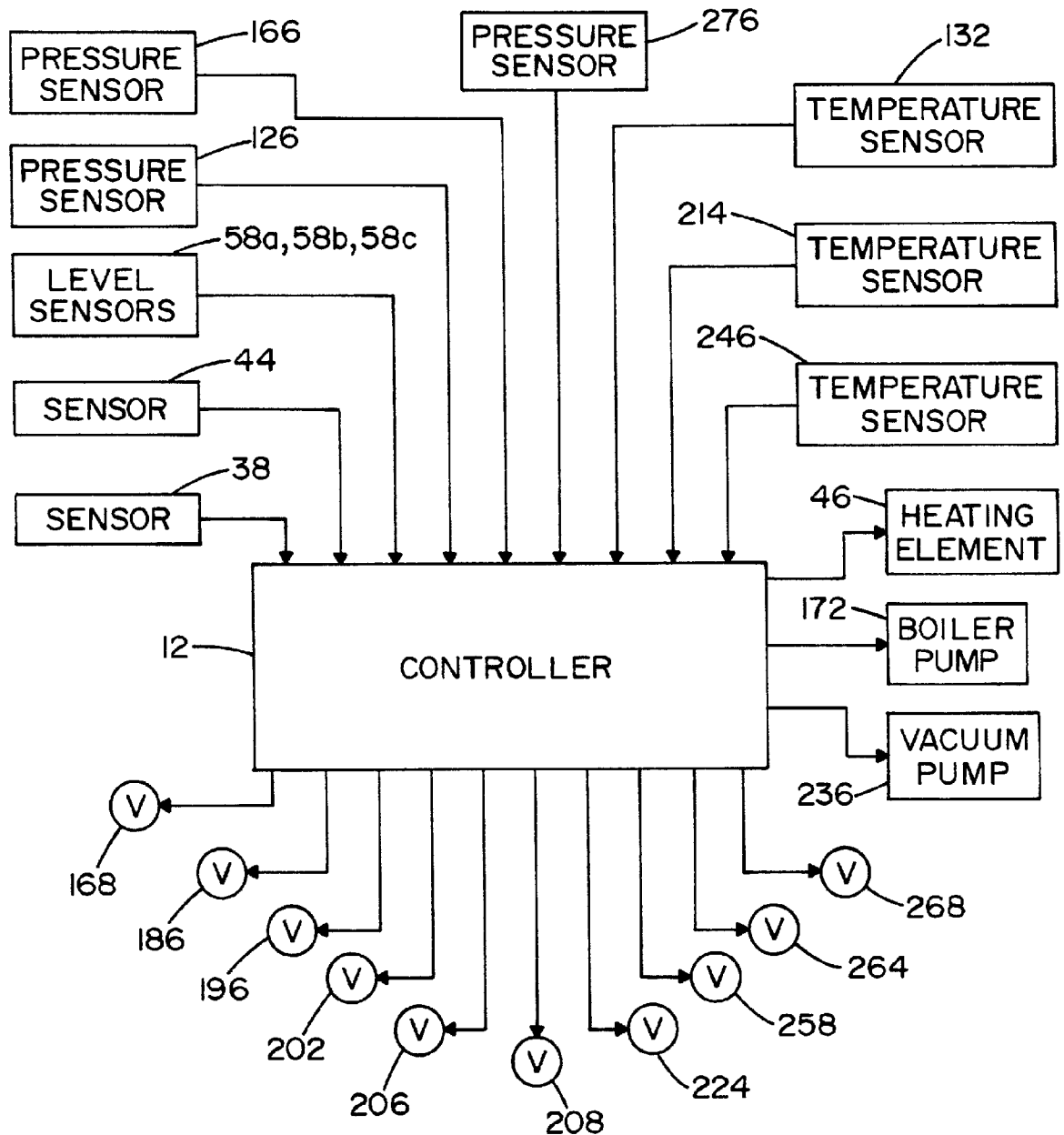
FIG. 3 is a schematic of a controller for the steam sterilizer shown in FIG. 1.

Sterilizer 10 includes a controller 12, schematically illustrated in FIG. 3, for controlling the operation of sterilizer 10. It is contemplated that sterilizer 10 may be designed and configured to rest upon a table or countertop or to be mounted into a self-supporting frame.

As shown in FIG. 1, sterilizer 10 is basically comprised of a vessel 20 and a fluid circuit 150. Vessel 20 includes an inner wall 24, an outer wall 26, a first end plate 32 and a second end plate 34. First end plate 32 is attached to one end of inner wall 24 and outer wall 26. Second end plate 34 is attached to another end of inner wall 24 and outer wall 26. Inner wall 24, first end plate 32 and second end plate 34 define a sterilization chamber 22 therebetween. Outer wall 26 is spaced from inner wall 24 such that inner wall 24, outer wall 26, first end plate 32 and second end plate 34 define an annular cavity 28 surrounding the periphery of sterilization chamber 22 (see FIG. 2). An opening 36 is formed in first end plate 32 to define an access to sterilization chamber 22.

A door 42 is mounted to first end plate 32 and is movable between an open position allowing access to chamber 22 and a closed positioned isolating chamber 22 from the surrounding environment. In the embodiment shown, door 42 and opening 36 are generally rectangular in shape.

A slot 92 is formed in the surface of first end plate 32 to extend around the periphery of opening 36. Slot 92 is dimensioned to receive a seal element 94. Seal element 94 is described in detail in U.S. patent application Ser. No. 12/414,176, incorporated herein by reference. A channel 96 extends through the bottom of first end plate 32 and communicates with the bottom of slot 92.

A sensor 38 is disposed in a lower portion of sterilization chamber 22. Sensor 38 provides an indication of whether there is water in the lower portion of sterilization chamber 22.

A sensor 44 is associated with door 42 to provide an indication of whether door 42 is in the open position or the closed position. In the embodiment shown, sensor 44 is a proximity sensor that is disposed outside sterilization chamber 22 adjacent to or near opening 36.

A heating element 46 is disposed in a lower portion of cavity 28. In the embodiment shown, heating element 46 extends through a lower portion of second end plate 34 of vessel 20. Heating element 46 is operable to heat water disposed in the lower portion of cavity 28. Heating element 46 is controllable by controller 12. In the embodiment shown, heating element 46 is a resistive heating element.

Figure 2:
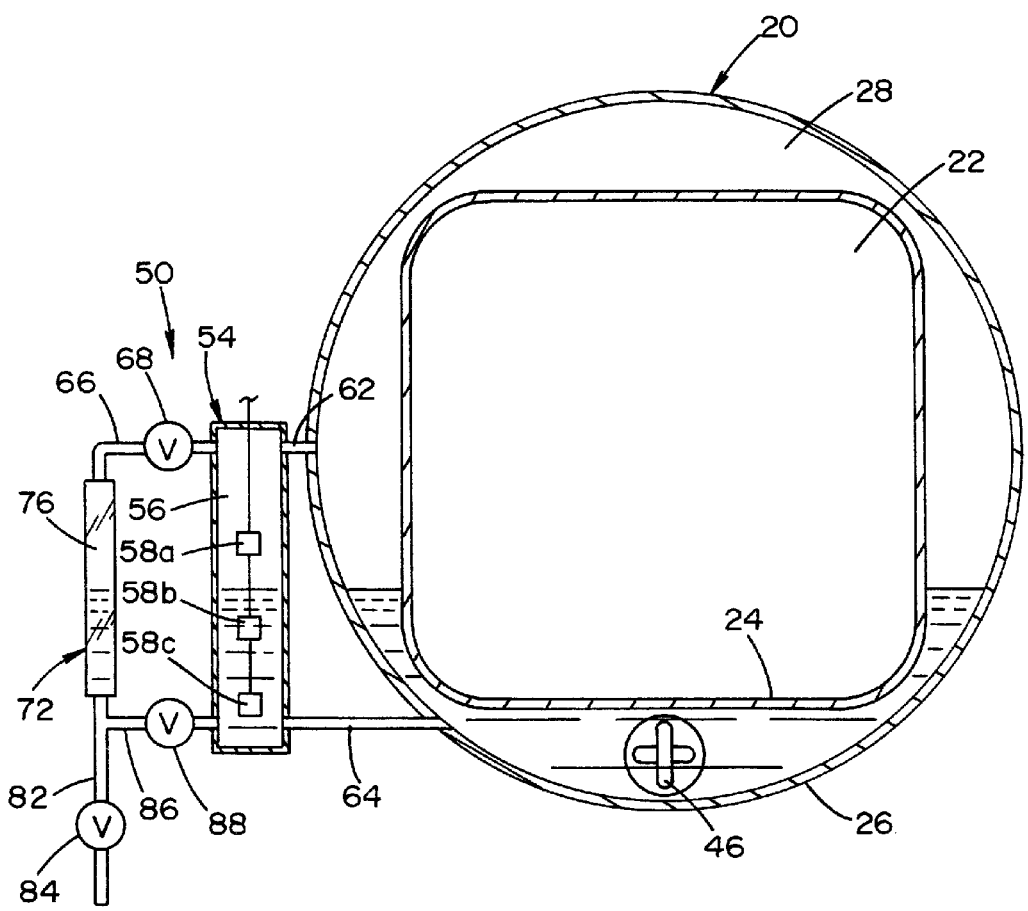
FIG. 2 is an enlarged, cross-sectional view showing a vessel of the steam sterilizer and a water level and sight glass assembly of the steam sterilizer.

As shown in FIG. 2, a water level and sight glass assembly 50 is attached to outer wall 26 of vessel 20. Water level and sight glass assembly 50 includes a housing 54 and a sight class 72. Housing 54 defines an internal cavity 56. Three (3) level sensors 58a, 58b, 58c are disposed within internal cavity 56. Level sensors 58a, 58b, 58c provide signals to controller 12 indicative of the level of water in internal cavity 56. Level sensor 58a is disposed near a top of cavity 56. Level sensor 58c is disposed near a bottom of cavity 56. Level sensor 58b is disposed midway between level sensor 58a and level sensor 58c. In the embodiment shown, each level sensor 58a, 58b, 58c is a capacitive-type sensor that provides a signal indicative of the presence or absence of water at a discrete level in internal cavity 56.

A conduit 62 is connected at one end to an upper portion of cavity 28 in vessel 20 and at another end to an upper portion of cavity 56 in housing 54. A conduit 64 is connected at one end to the lower portion of cavity 28 in vessel 20 at another end to a lower portion of cavity 56 in housing 54.

Sight glass 72 defines a cavity 76. Sight glass 72 includes at least one transparent wall for allowing a user to view the level of water within cavity 76.

A conduit 66 is connected at one end to the upper portion of cavity 56 in housing 54 and at another end to an upper portion of cavity 76 in sight glass 72. A valve 68 is disposed in conduit 66 to isolate cavity 76 in sight glass 72 for maintenance. Valve 68 is a manual valve. A conduit 82 is connected at one end to cavity 76 in sight glass 72 and at another end to a drain. A valve 84 is disposed in conduit 82 to drain cavity 76 in sight glass 72 for maintenance. Valve 84 is a manual valve.

A conduit 86 is connected at one end to the lower portion of cavity 56 in housing 54 and at another end to conduit 82. Conduit 86 is connected to conduit 82 at a location between valve 84 and sight glass 72. A valve 88 is disposed in conduit 86 to isolate cavity 76 in sight glass 72 for maintenance. Valve 88 is a manual valve.

Referring now to FIG. 1, a conduit 116 is connected at one end to outer wall 26 to provide fluid communication with the upper portion of cavity 28. A relief valve 118 is disposed at another end of conduit 116. Relief valve 118 is operable to allow fluid above a predetermined pressure to vent from cavity 28. A branch conduit 116a extends from conduit 116. A pressure gauge 122 is disposed at an end of branch conduit 116a. Pressure gauge 122 provides a visual indication of the pressure in cavity 28.

A conduit 124 fluidly communicates with sterilization chamber 22. In the embodiment shown, conduit 124 extends through outer wall 26 and is connected at one end to inner wall 24. A pressure sensor 126 is disposed at another end of conduit 124. Pressure sensor 126 provides a signal to controller 12 indicative of the pressure within sterilization chamber 22. A branch conduit 124a extends from conduit 124. A pressure gauge 128 is disposed at an end of branch conduit 124a. Pressure gauge 128 provides a visual indication of the pressure in sterilization chamber 22.

A temperature sensor 132 is fluidly connected to cavity 28. Temperature sensor 132 provides a signal to controller 12 indicative of the temperature in cavity 28. In the embodiment shown, a conduit is provided to fluidly connect temperature sensor 132 to the upper portion of cavity 28.

Fluid circuit 150 of sterilizer 10 is provided for conveying fluid to and from vessel 20. Fluid circuit 150 includes a water inlet assembly 160, a steam/air supply assembly 180, a drain assembly 220 and a cooling assembly 250.

Water inlet assembly 160 connects vessel 20 to a source of water. Water inlet assembly 160 is generally comprised of an inlet line 162, an inlet valve 164, a boiler pump 172 and a heat exchanger 174.

Inlet line 162 extends from a source of water to outer wall 26 to connect the source of water to the lower portion of cavity 28. In the embodiment shown, the source of water provides de-ionized water at a pressure of between about 10 psig to about 50 psig and at a temperature of at least 140° F.

Inlet valve 164 is disposed within inlet line 162 to control the flow of water into sterilizer 10. In the embodiment shown, inlet valve 164 is a manual valve that allows an operator to manually control the flow of water into sterilizer 10. A pressure sensor 166 is disposed in inlet line 162 at a location downstream of inlet valve 164. Pressure sensor 166 provides a signal to controller 12 indicative of the pressure of water in inlet line 162. A valve 168 is disposed in inlet line 162 at a location downstream of pressure sensor 166. Valve 168 is operable to control the flow of fluid into sterilizer 10. Valve 168 is controllable by controller 12.

Boiler pump 172 is disposed in inlet line 162. Boiler pump 172 is designed to provide water to sterilizer 10 at a predetermined pressure and flow rate. Boiler pump 172 is controllable by controller 12.

A portion of inlet line 162 extends through heat exchanger 174. A check valve 176 is disposed in inlet line 162 at a location between boiler pump 172 and heat exchanger 174. Check valve 176 is designed to restrict fluid from flowing from heat exchanger 174 to boiler pump 172.

Steam/air supply assembly 180 is provided for conveying steam from cavity 28 to sterilization chamber 22 and slot 92 and for conveying air to sterilization chamber 22. Assembly 180 is generally comprised of a chamber supply line 182, a seal supply line 198, a vent line 192 and valves 186, 196, 202 and filter 194.

A first end of chamber supply line 182 is connected to the upper portion of cavity 28. In the embodiment shown, the first end of chamber supply line 182 is connected to an upper portion of outer wall 26. A second end of chamber supply line 182 is connected to the upper portion of sterilization chamber 22. In the embodiment shown, the second end of chamber supply line 182 extends through outer wall 26 and is connected to the upper portion of inner wall 24. A plate 184 is located in sterilization chamber 22 immediately adjacent to the location where the second end of chamber supply line 182 is connected to the upper portion of inner wall 24.

Valve 186 is disposed in chamber supply line 182. Valve 186 is operable to control the flow of fluid therethrough. Valve 186 is controllable by controller 12.

Vent line 192 is connected to chamber supply line 182 between valve 186 and the second end of chamber supply line 182. One end of vent line 192 communicates with a source of air. Filter 194 is provided in vent line 192 to filter air flowing through vent line 192. Valve 196 is disposed downstream of filter 194. Valve 196 is operable to control the flow of air through vent line 192. Valve 196 is controllable by controller 12.

Seal supply line 198 provides steam from cavity 28 to slot 92. One end of seal supply line 198 is connected to chamber supply line 182 at a location between the first end of chamber supply line 182 and valve 186. A second end of seal supply line 198 is connected to channel 96 in first end plate 32.

Valve 202 is disposed in seal supply line 198. Valve 202 is operable to control the flow of fluid therethrough. Valve 202 is controllable by controller 12.

Drain assembly 220 is connected to sterilization chamber 22 and steam/air supply assembly 180 for draining fluid from chamber 22 and slot 92. Drain assembly 220 is generally comprised of a line 204, a first conduit 222, a second conduit 232, a drain tank 242, a heat exchanger 234 and a vacuum pump 236.

A first end of line 204 is connected to seal supply line 198 at a location between valve 202 and the second end of seal supply line 198. A second end of line 204 is connected to a lower portion of sterilization chamber 22. In the embodiment shown, the second end of line 204 extends through outer wall 26 and is connected to the lower portion of inner wall 24.

Valve 206 is disposed in line 204. Valve 206 is operable to control the flow of fluid therethrough. Valve 206 is controllable by controller 12.

Valve 208 is disposed in line 204 between valve 206 and the second end of line 204. Valve 208 is operable to control the flow of fluid therethrough. Valve 208 is controllable by controller 12.

A restrictor 212 is disposed in line 204 between valve 206 and the first end of line 204. Restrictor 212 is provided to control the rate that fluid may flow therethrough.

A temperature sensor 214 is connected to line 204 at a location between valve 208 and the second end of line 204. Temperature sensor 214 provides a signal to controller 12 indicative of the temperature of the fluid flowing along that portion of line 204.

First conduit 222 extends from line 204 to drain tank 242. In particular, one end of first conduit 222 is connected to line 204 at a location between valve 208 and the second end of line 204. A portion of first conduit 222 extends through heat exchanger 174.

A valve 224 is disposed in first conduit 222 at location between the end of first conduit 222 that is connected to line 204 and the portion of first conduit 222 that passes through heat exchanger 174. Valve 224 is operable to control the flow of fluid through first conduit 222. Valve 224 is controllable by controller 12.

A flow restrictor 226 is disposed in first conduit 222 to control the rate that fluid may flow through first conduit 222. Flow restrictor 226 is disposed between valve 224 and heat exchanger 174.

Second conduit 232 of drain assembly 220 extends from line 204 to drain tank 242. In particular, one end of second conduit 232 is connected to line 204 at a location between valve 206 and valve 208. A portion of second conduit 232 extends through heat exchanger 234.

Vacuum pump 236 is disposed in second conduit 232 at a location between heat exchanger 234 and tank 242. Vacuum pump 236 is operable to draw fluid from the portion of second conduit 232 upstream of vacuum pump 236 and to exhaust the fluid into tank 242. Vacuum pump 236 is controllable by controller 12.

A line 244 extends from an upper portion of drain tank 242 to a drain (not shown). A temperature sensor 246 is attached to drain tank 242. Temperature sensor 246 provides a signal to controller 12 indicative of the temperature of the fluid in drain tank 242.

Cooling assembly 250 is connected to drain assembly 220 for cooling fluid conveyed along second conduit 232 of drain assembly 220. Cooling assembly 250 is generally comprised of a line 252, a valve 254, a conduit 256 and a bypass conduit 266.

Line 252 is connected at one end to source of cooling fluid and at another end to second conduit 232 of drain assembly 220 at a location between vacuum pump 236 and tank 242. In the embodiment shown, the source of cooling fluid provides water at 20-50 psig, 15 gallons per minute at a temperature of about 70° F. A portion of line 252 extends through heat exchanger 234.

Valve 254 is disposed in line 252 to control the flow of cooling fluid therethrough. In the embodiment shown, valve 254 is a manual valve that allows an operator to manually control the flow of fluid through line 252.

Conduit 256 extends between line 252 and vacuum pump 236. A valve 258 is disposed in conduit 256 to control the flow of cooling fluid along conduit 256. A flow restrictor 262 is disposed in conduit 256 at a location between valve 258 and vacuum pump 236. Flow restrictor 262 is designed to control the rate that cooling fluid may flow along conduit 256 and to vacuum pump 236.

A valve 264 is disposed in line 252 at a location between conduit 256 and heat exchanger 234. Valve 264 is operable to control the flow of cooling fluid therethrough. Valve 264 is controllable by controller 12.

Bypass conduit 266 is attached to line 252 to bypass valve 264. In particular, the first end of bypass conduit 266 is connected to line 252 at a location between valve 264 and the location where conduit 256 is connected to line 252. The second end of bypass conduit 266 is connected to line 252 at a location between valve 264 and heat exchanger 234.

A valve 268 is disposed in bypass conduit 266 to control the flow of fluid along bypass conduit 266. Valve 268 is controllable by controller 12. A flow restrictor 272 is disposed in bypass conduit 266 at a location between bypass valve 268 and the second end of bypass conduit 262. Flow restrictor 272 is provided to control the rate that fluid that may flow along bypass conduit 266.

A conduit 274 is connected to line 252 at a location between valve 264 and the location wherein the first end of bypass conduit 266 is connected to line 252. A pressure sensor 276 is disposed at an end of conduit 274. Pressure sensor 276 provides a signal to controller 12 indicative of the pressure of fluid in conduit 274. A flow restrictor 278 is disposed in conduit 274. Flow restrictor 278 is provided to restrict the amount of cooling fluid that may flow along conduit 274.

As illustrated schematically in FIG. 3, controller 12 communicates with sensors 38, 44, level sensors 58a, 58b, 58c, pressure sensors 126, 166, 276 and temperature sensors 132, 214, 246. Controller 12 is connected to valves 168, 186, 196, 202, 206, 208, 224, 258, 264, 268 to control the position of the aforementioned valves. Controller 12 is connected to heating element 46, boiler pump 172 and vacuum pump 236 to control the operation thereof, as described below.

Prior to initializing a sterilization cycle, valve 164 is in the open position and controller 12 initiates the filling of cavity 28 by causing valve 168 to move to the open position such that water may flow to boiler pump 172. Controller 12 then energizes boiler pump 172 so that pressurized water is conveyed through heat exchanger 174 and into a lower portion of cavity 28. As water fills cavity 28, water also fills cavities 56, 76 of water level and sight glass assembly 50. The level of water in cavity 56, 76 of water level and sight glass assembly 50 will be similar to the level of water in cavity 28. The water continues to fill cavity 28 until the level of the water in cavity 56, as determined by level switches 58a, 58b, 58c, reaches a predetermined "fill" level. Controller 12 then de-energizes boiler pump 172 and causes valve 168 to move to the closed position so that water ceases to flow into cavity 28.

Controller 12 is programmed to continuously monitor level sensors 58a, 58b, 58c. In this respect, if the water level in cavity 56 of water level and sight glass assembly 50, i.e., essentially the water level in cavity 28, drops to below a predetermined level, level sensors 58a, 58b, 58c will provide a signal to controller 12 that indicates such an event. Controller 12 then will energize boiler pump 172 and move valve 168 to the open position thereby allowing water to enter cavity 28 and water level and sight glass assembly 50. When a desired water level is reached within cavity 56, as determined by level sensors 58a, 58b, 58c, controller 12 de-energizes boiler pump 172 and causes valve 168 to move back to the closed position so that water ceases to fill cavity 28.

After the level of water in cavity 28 is at the desired "fill" level, controller 12 will initiate a steam generation phase. Controller 12 energizes heating element 46 so that the water in the lower portion of cavity 28 is heated and vaporized to produce steam. To prevent cavity 28 from becoming over pressurized, relief valve 118 is designed to move to an open position when the pressure in cavity 28 exceeds a predetermined maximum pressure to vent steam from cavity 28. Cavity 28 is maintained with pressurized steam regardless of whether a sterilization cycle is being performed. Cavity 28 is designed to be emptied once a day to flush contaminates and sediment therefrom. Thereafter, cavity 28 is refilled with water and steam is generated within cavity 28 in preparation for a sterilization cycle.

Referring now to FIGS. 1-2, the operation of sterilizer 10 shall now be described with reference to sterilizing items disposed in chamber 22. Prior to initiating a sterilization cycle, a user opens door 42 and inserts medical instruments and/or devices to be sterilized into sterilization chamber 22. The user then closes door 42. Sensor 44 provides a signal to controller 12 indicative of whether door 42 is in the closed position. Once controller 12 determines that door 42 is in the closed position, controller 12 causes valve 202 to move to the open position such that steam is conveyed from cavity 28 to the cavity defined between seal element 94 and slot 92. The pressurized steam causes seal element 94 to sealingly engage door 42 thereby sealing sterilization chamber 22 from the surrounding environment. Controller 12 then controls sterilizer 10 through a sterilization cycle. Prior to the initiation of the sterilization cycle, manual valve 254 is in an open position and controller 12 causes valves 168, 186, 196, 202, 206, 208, 224, 258, 264 and 268 to be in a closed position. Controller 12 also causes vacuum pump 236 to be de-energized.

Controller 12 initiates the evacuation of air from chamber 22 by causing valves 208, 258 to move to the open position and energizing vacuum pump 236. Vacuum pump 236 draws air from sterilization chamber 22, through a portion of line 204 and through second conduit 232. Vacuum pump 236 then exhausts the air through second conduit 232 and into drain tank 242. Vacuum pump 236 continues to draw air out of sterilization chamber 22 until the pressure within sterilization chamber 22, as measured by pressure sensor 126, is at a desired pressure. Controller 12 then de-energizes vacuum pump 236 and causes valves 208, 258 to move to the closed position.

Once the pressure in sterilization chamber 22 is at the desired pressure, controller 12 causes valve 186 in chamber supply line 182 to move to the open position thereby allowing steam to be conveyed from cavity 28, through chamber supply line 182 and into sterilization chamber 22. According to the present invention chamber supply line 182 is designed to be as short as possible to limit the amount of heat loss to the surrounding environment.

Controller 12 is programmed such that steam continues to fill chamber 22 until the pressure in chamber 22, as measured by pressure sensor 126, is at a predetermined pressure. During the steam sterilization cycle, controller 12 controls valve 224 so that a desired amount of steam may be vented from sterilization chamber 22 during the steam sterilization cycle. In this respect, temperature sensor 214 in line 204 provides a signal to controller 12 indicative of the temperature of the steam in sterilization chamber 22. The pressurized steam within chamber 22 is maintained at a predetermined temperature for a predetermined period of time sufficient to sterilize instruments and/or devices within chamber 22. Sensor 38 provides a signal to controller 12 indicative of whether there is water in the lower portion of sterilization chamber 22. If sensor 38 detects water in the lower portion of sterilization chamber 22, controller 12 will sound an alarm and abort the steam sterilization cycle.

Throughout the steam sterilization cycle, the pressure sensors and temperature sensors monitor the operational conditions of sterilizer 10 to ensure proper functioning thereof. Once the steam sterilization cycle is complete, controller 12 causes valve 186 to move to the closed position. Controller 12 then causes valve 208 in line 204 to move to the open position.

Controller 12 initiates the removal of steam from chamber 22 by energizing vacuum pump 236 and causing valve 258 to move to the open position. Vacuum pump 236 draws steam from chamber 22 and exhausts the steam through second conduit 232 and into drain tank 242. Valve 258 allows cooling fluid to flow to the head of vacuum pump 236 to cool vacuum pump 236.

Controller also controls valves 264, 268 such that cooling fluid may be conveyed through heat exchanger 234. The amount of cooling fluid required is determined based on the amount of cooling fluid needed to cause the steam drawn from chamber 22 to condense to water. After the steam is withdrawn from chamber 22, pump 236 continues to run to draw a vacuum on chamber 22 to assist in removing moisture therefrom.

After a vacuum is drawn on chamber 22, controller 12 de-energizes vacuum pump 236 and causes valve 208 to move to the closed position. Controller 12 then causes valve 196 to move to the open position such that air is drawn into chamber 22. In particular, air is drawn through vent line 192, through filter 194 and into chamber 22. The incoming air is conveyed through filter 194 so that only filtered air is allowed to replace the steam that is drawn from chamber 22. In this respect, filter 194 prevents contamination from entering chamber 22.

After the pressure within sterilization chamber 22 reaches a predetermined pressure, controller 12 causes valves 206, 258, 264, 268 to move to an open position and energizes vacuum pump 236. Steam in the cavity defined between seal element 94 and slot 92 is then drawn through seal supply line 198, through a portion of line 204 and through second conduit 232 to vacuum pump 236. Vacuum pump 236 exhausts the steam through second conduit 232 and into drain tank 242. As the steam is withdrawn from the cavity defined between seal element 94 and slot 92, seal element 94 disengages from door 42. Once seal element 94 disengages from door 42, controller 12 de-energizes vacuum pump 236 and causes valves 206, 258, 264, 268 to move to the closed position. Controller 12 then allows the user access to chamber 22 to remove the instruments and/or devices disposed therein.

As described in detail above, the present invention provides a steam sterilizer wherein a heating element is disposed in a cavity surrounding a sterilization chamber. The heating element is provided to vaporize water within the cavity to produce steam. A portion of the heat generated by the heating element is conducted into the sterilization chamber. In this respect, the present invention provides a steam sterilizer that makes efficient use of energy during a steam sterilization cycle.

The foregoing description is a specific embodiment of the present invention. It should be appreciated that this embodiment is described for purposes of illustration only, and that numerous alterations and modifications may be practiced by those skilled in the art without departing from the spirit and scope of the invention. It is intended that all such modifications and alterations be included insofar as they come within the scope of the invention as claimed or the equivalents thereof.

Having described the invention, the following is claimed:

1. A steam sterilizer for sterilizing instruments and devices, said sterilizer comprised of:
    a vessel having an inner wall and an outer wall, said inner wall defining a sterilization chamber, said outer wall spaced from said inner wall to define a cavity surrounding said sterilization chamber;
    a heating element disposed in a lower portion of said cavity, said heating element for vaporizing fluid in said cavity; and
    a fluid circuit connected to said vessel, said fluid circuit for conveying fluid to said cavity, for conveying steam from said cavity to said sterilization chamber and for exhausting steam from said sterilization chamber, said fluid circuit including:
    a conduit fluidly connecting said sterilization chamber to said cavity,
    a valve disposed in said conduit for controlling the flow of steam from said cavity to said sterilization chamber,
    a boiler pump for conveying a fluid to said cavity of said vessel;
    a heat exchanger;
    a first line for draining steam from said sterilization chamber, a portion of said first line extending through said heat exchanger; and
    a second line fluidly connecting said boiler pump to said cavity, a portion of said second line extending through said heat exchanger wherein heat is transferred between steam in said first line and fluid in said second line.

2. A steam sterilizer as defined in claim 1, wherein said fluid circuit further comprises:
    a heat exchanger;
    a first line for draining steam from said sterilization chamber, a portion of said first line extending through said heat exchanger; and
    a second line for conveying a cooling fluid therethrough, a portion of said second line extending through said heat exchanger wherein heat is transferred between steam in said first line and cooling fluid in said second line.

3. A steam sterilizer as defined in claim 1, wherein said fluid circuit further comprises:
    a vacuum pump for removing steam from said sterilization chamber.

4. A steam sterilizer as defined in claim 1, wherein said fluid circuit further comprises:
    a line for conveying steam from said cavity to a seal assembly disposed in said vessel, said line fluidly connected at one end to said cavity and at another end to said seal assembly.

* * * * *